(12) United States Patent
Schiendorfer

(10) Patent No.: US 7,544,825 B1
(45) Date of Patent: Jun. 9, 2009

(54) PREPARATION OF SILOXY-BRIDGED METALLOCENES

(75) Inventor: Michael Schiendorfer, Frankfurt (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 12/157,802

(22) Filed: Jun. 12, 2008

(51) Int. Cl.
  *C07F 17/00* (2006.01)
  *C07F 7/00* (2006.01)

(52) U.S. Cl. .......................... 556/11; 556/12; 556/457
(58) Field of Classification Search ................ 556/11, 556/12, 457
  See application file for complete search history.

(56) References Cited

U.S. PATENT DOCUMENTS

| | | | |
|---|---|---|---|
| 5,153,157 A | 10/1992 | Hlatky et al. |
| 5,198,401 A | 3/1993 | Turner et al. |
| 5,241,025 A | 8/1993 | Hlatky et al. |
| 5,278,264 A | 1/1994 | Spaleck et al. |
| 5,414,180 A | 5/1995 | Geerts et al. |
| 5,539,124 A | 7/1996 | Etherton et al. |
| 5,637,659 A | 6/1997 | Krishnamurti et al. |
| 5,648,440 A | 7/1997 | Sugano et al. |
| 5,902,866 A | 5/1999 | Nagy et al. |
| 6,211,311 B1 | 4/2001 | Wang et al. |
| 6,316,556 B1 | 11/2001 | Kallio et al. |
| 6,440,889 B1 | 8/2002 | Tsuie |
| 6,872,843 B2 | 3/2005 | Schottek et al. |
| 7,037,872 B2 | 5/2006 | Aubert et al. |
| 7,060,765 B2 | 6/2006 | Vaughan et al. |
| 7,074,863 B2 | 7/2006 | Ekholm et al. |
| 7,109,278 B2 | 9/2006 | Okumura et al. |
| 7,122,498 B2 * | 10/2006 | Hart et al. .................. 502/152 |

OTHER PUBLICATIONS

Reybuck, et al., "Ethylene/1-Hexene Copolymerization with Tetramethyldisiloxane-Bridged Bis(indenyl) Metallocenes", *J. Polym. Sci. A* 42 (2004) 3323.
Leino, et al., "Isospecific Propylene Polymerization with a Novel 2-Substituted Bis(indenyl) *ansa*-Zirconocene", *Organometallics* 15 (1996) 2450.
Jordan, et al., "Efficient Synthesis of *rac*-(Ethylenebis(indenyl))ZrX₂ Complexes via Amine Elimination", *Organometallics* 14 (1995) 5.
Jordan, et al., "Synthesis of Group 4 Metal *rac*-(EBI)M(NR₂)₂ Complexes by Amine Elimination. Scope and Limitations", *Organometallics* 15 (1996) 4030, 4038, 4045.
Diamond, et al., Efficient Synthesis of Chiral *ansa*-Metallocenes by Amine Elimination. Synthesis, Structure, and Reactivity of *rac*-(EBI)Zr(NMe₂)₂ *J. Am. Chem. Soc.* 118 (1996) 8024.

* cited by examiner

*Primary Examiner*—Porfirio Nazario Gonzalez
(74) *Attorney, Agent, or Firm*—Jonathan L. Schuchardt

(57) ABSTRACT

A method for making siloxy-bridged ligand precursors and metallocene complexes is disclosed. Indanone enolates react with cyclopentadienylsilyl compounds to produce ligand precursors, which are reacted with a Group 3-10 transition metal source to generate metallocene complexes. The method provides simple, regioselective access to particular siloxy-bridged metallocenes starting from easily elaborated indanones.

14 Claims, No Drawings

PREPARATION OF SILOXY-BRIDGED METALLOCENES

FIELD OF THE INVENTION

The invention relates to siloxy-bridged metallocenes and a method for making them. The metallocenes are valuable catalyst components for olefin polymerization.

BACKGROUND OF THE INVENTION

Metallocenes and other single-site complexes provide polyolefins with interesting physical properties that can be tailored to meet the needs of a particular application. They complement traditional Ziegler-Natta catalysts, which have multiple active sites and provide polymers with different attributes.

Metallocenes contain two cyclopentadienyl ("Cp") or Cp-like ligands that coordinate through π-bonding to a transition metal, and the ligands are frequently linked via a divalent bridging group such as dialkylsilyl, methylene, or the like. Metallocenes in which the bridging group contains a siloxy (—Si—O—) moiety have been described, at least generally, although ways to prepare them are not disclosed. See, e.g., U.S. Pat. Nos. 7,109,278 and 5,278,264.

Other varieties of metallocenes incorporate a disiloxane bridge, in which an oxygen bridges two silacyclopentadienyl groups (see U.S. Pat. No. 7,060,765 and *J. Polym. Sci. A* 42 (2004) 3323). The disiloxy-bridged complexes are typically made by reacting indenyllithium with dichlorotetramethyldisiloxane; they cannot be made directly from indanone enolates. Metallocenes that include siloxy substituents that are not part of the bridging group are also known (see U.S. Pat. Nos. 7,074,863; 7,037,872; and 6,316,556; and *Organometallics* 15 (1996)2450). In other non-metallocene complexes, the siloxy bridge is part of a "constrained geometry" complex (see U.S. Pat. No. 7,074,863 at col. 13) or is joined to a non-Cp group (see U.S. Pat. No. 6,872,843). In the '843 patent, the siloxy-bridged complex is made by reacting an indenylchlorodimethylsilane with an aldimine-functionalized phenoxide salt derived from salicylaldehyde.

References that generally disclose siloxy-bridged metallocenes (such as the '278 and '264 patents noted earlier) do not teach how to make them. Interestingly enough, these same references illustrate that indanones are commonly converted to indenes in the early stages of making bridged ligand precursors and transition metal complexes that incorporate the precursors. (See, for example, the '278 patent at Examples 1e, 2d, and 3e; and the '264 patent at Examples I.3; II.2; and III.3; see also U.S. Pat. No. 7,074,863 at cols. 8-28.) Thus, the indanone is usually converted to an alcohol by reduction or Grignard addition, followed by acid-catalyzed dehydration to provide an indene. The indene is then further elaborated to make the bridged ligand precursor.

Preparation of Bridged Metallocene Complexes from Indenes, Particularly substituted indenes, is further complicated by the possibility of making multiple regioisomers. Consider, for instance, the simple case of 2,4-dimethylindene, which provides two different stereoisomers in the following reaction:

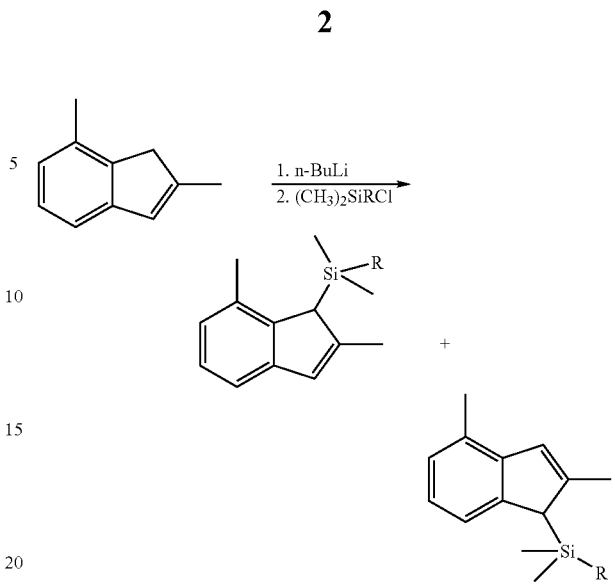

Because deprotonation gives two different indenides, halide displacement can occur at either of two carbons. Such stereoisomers are not usually easy to separate, so the catalysts ultimately made will be mixtures of different compounds; this defeats the purpose of having a "single-site" catalyst. Conversely, substituents on the indene are often considered valuable for influencing catalyst activity or polymer properties. Thus, indenes are not optimum starting materials for making metallocenes.

In sum, there is a continuing need for efficient ways to make bridged metallocene complexes. A valuable approach would be simple to practice with readily available reagents and would avoid the multistep approach now used commonly to make indenyl complexes. Ideally, the method would utilize readily available indanones as starting materials, including substituted indanones, and would enable an efficient synthesis of bridged ligand precursors and transition metal complexes while maintaining control over regiochemical outcome.

SUMMARY OF THE INVENTION

In one aspect, the invention relates to siloxy-bridged metallocene complexes and a method for making them. The method comprises two steps. First, an indanone enolate reacts with a cyclopentadienylsilyl compound to produce a ligand precursor. In a second step, the precursor reacts with a transition metal source to produce the metallocene complex. The invention also includes a method for making a siloxy-bridged ligand precursor from an indanone enolate. The invention provides simple, regioselective access to particular siloxy-bridged metallocenes and ligand precursors, and it uses readily available, easily elaborated indanones as starting materials.

DETAILED DESCRIPTION OF THE INVENTION

Siloxy-bridged metallocene complexes of the inventive method are made from indanone enolates. Indanone enolates are salts made by deprotonating indanones that have at least one enolizable hydrogen, i.e., at least one hydrogen on a carbon atom (an "α-carbon") that is bonded to the indanone carbonyl group. The simplest indanones are 1-indanone and 2-indanone. Deprotonation with a strong base, e.g., with lithium diisopropylamide, usually at low temperature provides the corresponding lithium enolates:

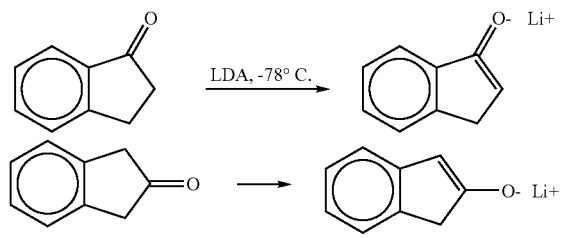

Suitable indanones have at least one hydrogen on a cyclopentanone carbon in addition to the enolizable hydrogen. This hydrogen is ultimately removed when a ligand precursor is converted into a siloxy-bridged metallocene complex. Otherwise, the indanone can have a variety of substituents commonly used in the art to regulate catalyst activity or fine-tune polymer physical or mechanical properties. Thus, any of the benzene or other ring carbons can be substituted or unsubstituted, and any pair of adjacent substituents can be joined to form a fused carbocyclic or heterocyclic ring.

Thus, suitable indanones include, for example, 1-indanone, 2-indanone, 2-methyl-1-indanone, 3-ethyl-1-indanone, 2-phenyl-1-indanone, 4-methyl-1-indanone, 5-isopropyl-1-indanone, 6-chloro-2-indanone, 4-methoxy-6-methyl-1-indanone, 4-trifluoromethyl-1-indanone, 7-bromo-2-indanone, and the like.

Preferred indanones have the general structure:

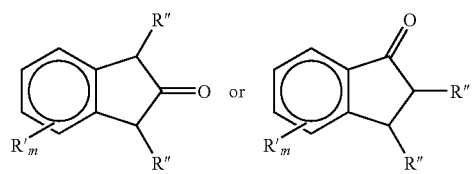

in which each R' is independently hydrocarbyl, halocarbyl, halide, amino, nitro, thioalkyl, alkoxy, or hydroxy; each R" is independently hydrogen, hydrocarbyl, halocarbyl, halide, amino, nitro, thioalkyl, alkoxy, or hydroxy; any pair of R' or R" substituents may be joined to form a 4-, 5-, 6-, or 7-membered carbocyclic or heterocyclic ring, and m has a value from 0 to 4.

Indanones are converted to the corresponding indanone enolates by any desired deprotonation method, and suitable methods are well known to those skilled in the art. Usually, a strong base such as lithium diisopropylamide (LDA), lithium isopropylcyclohexylamide (LICA), lithium 2,2,6,6-tetramethylpiperidide (LTMP), lithium hexamethyldisilazide (LHMDS), sodium hydride, potassium hydride, potassium t-butoxide, n-butyllithium, or the like is used. Preferably, the deprotonation is performed by carefully combining about one equivalent of the base and indanone at low temperature (room temperature or below) under an inert atmosphere in a suitable dry solvent (e.g., hydrocarbon, ether). The resulting enolate is normally used immediately in the next reaction step, i.e., it is usually not stored.

The indanone enolate reacts with a cyclopentadienylsilyl compound to produce a ligand precursor. The cyclopentadienylsilyl compound has a cyclopentadiene or substituted cyclopentadiene moiety bonded to silicon. Also attached to silicon is a "leaving group," i.e., a group that can be displaced by the oxygen anion of an indanone enolate. The cyclopentadiene moiety has one acidic hydrogen, removal of which generates a cyclopentadienide. Any of the four carbons not attached to silicon can be substituted, and any two adjacent carbons can be joined to form a 4-, 5-, 6-, or 7-membered ring. Thus, the cyclopentadienylsilyl compound can comprise a substituted or unsubstituted cyclopentadienyl, indenyl, fluorenyl, or thiophene-fused cyclopentadienyl group, or the like.

Preferred cyclopentadienylsilyl compounds have the structure:

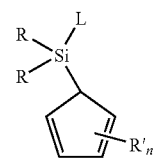

in which L is a leaving group, each R is independently a $C_1$-$C_{20}$ hydrocarbyl, and each R' is independently hydrocarbyl, halocarbyl, halide, amino, nitro, thioalkyl, alkoxy, or hydroxy. Any pair of R or R' substituents may be joined to form a 4-, 5-, 6-, or 7-membered carbocyclic or heterocyclic ring; n has a value from 0 to 4 Suitable L groups include, for example, halides, carboxylates (acetates, triflates), sulfonates (tosylates, mesylates), and the like. Specific examples include chloride, bromide, iodide, triflate, tosylate, p-nitrobenzenesulfonate, mesylate, trifluoroacetate, and p-nitrobenzoate.

A few exemplary cyclopentadienylsilyl compounds:

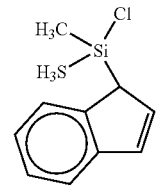

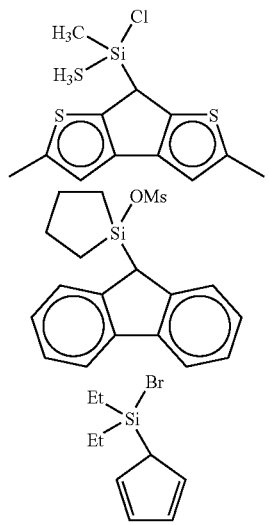

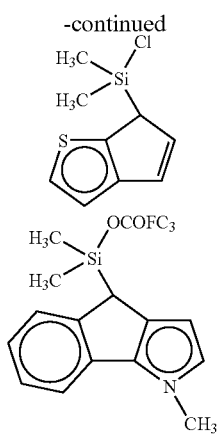

Reaction of an indanone enolate and the cyclopentadienylsilyl compound provides a siloxy-bridged ligand precursor. This reaction is typically performed by combining approximately equimolar amounts of the indanone enolate and the cyclopentadienylsilyl compound under conditions effective to displace the leaving group from the cyclopentadienylsilyl compound and generate the siloxy-bridged ligand precursor. Usually, the reactants are combined at room temperature or below in the presence of a dry organic solvent (tetrahydrofuran, toluene, hexanes, or the like), preferably under an inert atmosphere (nitrogen, argon, etc.) and stirred until the reaction is complete. The product is conveniently isolated in a typical organic workup and purified, if desired, by any suitable means (short-path distillation, column chromatography, crystallization).

Some ligand precursors have the structure:

wherein each R is independently a $C_1$-$C_{20}$ hydrocarbyl, each R' is independently hydrocarbyl, halocarbyl, halide, amino, nitro, thioalkyl, alkoxy, or hydroxy; each R" is independently hydrogen, hydrocarbyl, halocarbyl, halide, amino, nitro, thioalkyl, alkoxy, or hydroxy; any pair of R, R', or R" substituents may be joined to form a 4-, 5-, 6-, or 7-membered carbocyclic or heterocyclic ring; and each of m and n has a value from 0 to 4.

The ligand precursor is converted to a siloxy-bridged metallocene complex using techniques that are known to those skilled in the art. In one convenient approach, the ligand precursor is doubly deprotonated, preferably at low temperature, and the resulting dianion reacts with a Group 3-10 transition metal source to provide the desired siloxy-bridged metallocene complex. The dianion route is advantageous; however, separate mono-deprotonation and reaction steps can be performed sequentially instead. In yet another convenient method known as "amine elimination," the Group 3-10 transition metal complex incorporates dialkylamino groups, and simply heating the precursor and complex together eliminates an amine and provides the desired siloxy-bridged metallocene complex. See U.S. Pat. No. 6,440,889, the teachings of which are incorporated herein by reference. See also R. Jordan et al., *Organometallics* 14 (1995) 5; *Organometallics* 15 (1996) 4030, 4038, 4045; and *J. Am. Chem. Soc.* 118 (1996) 8024.

Dianion generation and reaction is illustrated as follows:

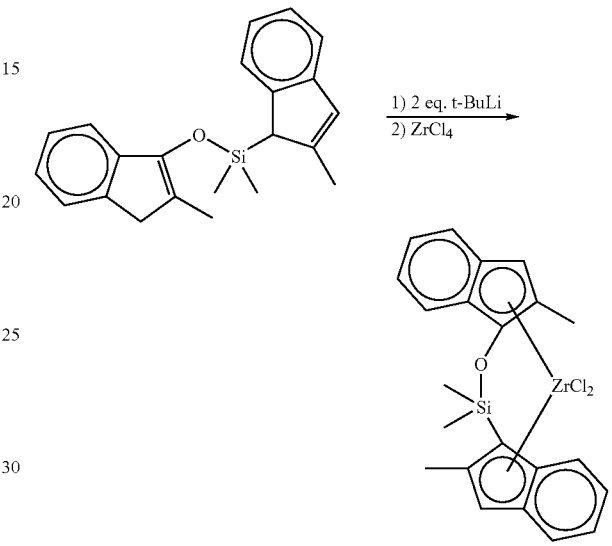

Amine elimination:

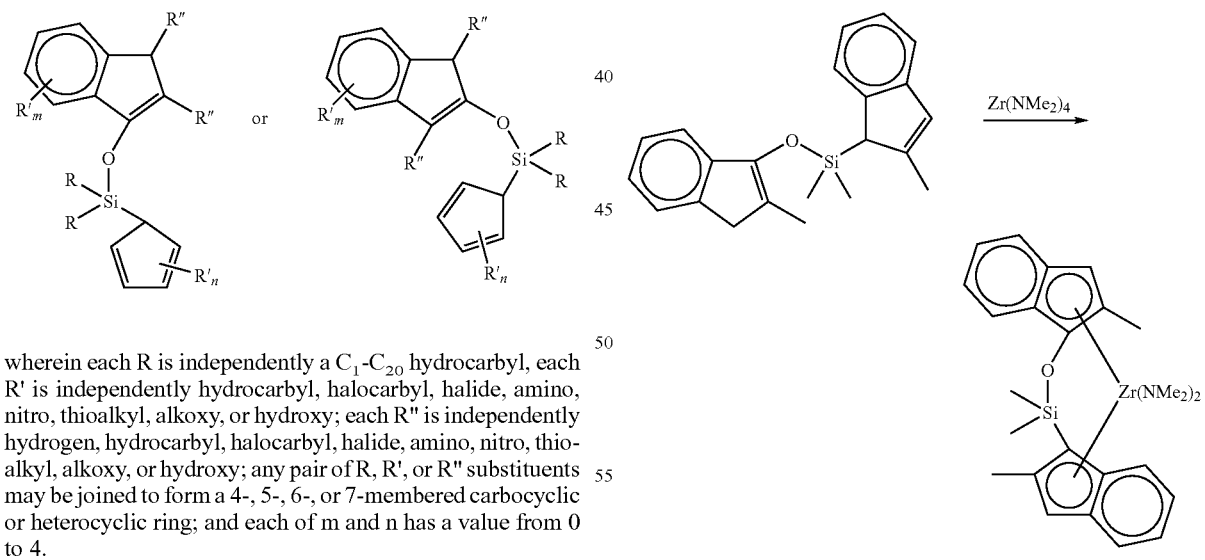

Deprotonation of ligand precursors is preferably performed using a sterically hindered base. Suitable sterically hindered bases are basic enough to abstract a proton from a cyclopentadiene moiety, but not nucleophilic enough to attack the silicon of the siloxy-bridged ligand precursor. I surprisingly found that ligand precursors can be successfully deprotonated using tert-butyllithium, but n-butyllithium attacks silicon, breaks the siloxy bond, and regenerates the indanone enolate (see Comparative Example 7). Suitable bases have a conjugate acid for which the acid has pKa>16. Examples include tert-butyllithium, sec-butyllithium, LDA, LICA, LTMP, LHMDS, potassium t-butoxide, and the like. t-Butyllithium is particularly preferred.

The ligand precursor reacts with a Group 3-10 transition metal source to produce the siloxy-bridged complex. Suitable transition metal sources include a Group 3 to 10 transition or lanthanide metal, preferably a Group 4 to 6 transition metal, and more preferably a Group 4 transition metal. The transition metal usually incorporates labile ligands that are easily displaced by cyclopentadienide ligands. Examples include halides, alkoxides, dialkylamines, alkyls, or other labile ligands. Halides such as $TiCl_4$ or $ZrCl_4$ are readily available, cost-effective, and particularly preferred.

Reacting the ligand precursor and the Group 3-10 transition metal source is normally routine, and the workup is usually minimal. Often, it suffices to prepare a solution or slurry of the metal source in a dry solvent and then combine it with the deprotonated ligand precursor, followed by stirring under ambient conditions until the reaction is complete. The complex is isolated by any convenient means, such as filtration.

When amine elimination is used to make the complex, there is no deprotonation step. Instead, an alkylamino-substituted transition metal compound, such as, e.g., tetrakis(dimethylamino)zirconium, is heated with the ligand precursor, typically in the presence of a solvent (hydrocarbon, halocarbon, ether, or the like). An inert gas (nitrogen, argon, etc.) is usually sparged into the mixture to assist in removing the resulting dialkylamine by-product (see, e.g., U.S. Pat. No. 6,440,889).

The method can be used to prepare a wide variety of siloxy-bridged complexes. Some of the siloxy-bridged metallocene complexes have the structure:

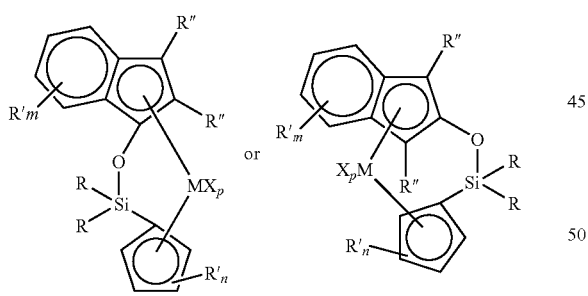

wherein M is a Group 3-10 transition metal, each X is independently halide, hydrocarbyl, alkoxy, dialkylamino, or siloxy; each R is independently $C_1$-$C_{20}$ hydrocarbyl, each R' is independently hydrocarbyl, halocarbyl, halide, amino, nitro, thioalkyl, alkoxy, or hydroxy; each R" is independently hydrogen, hydrocarbyl, halocarbyl, halide, amino, nitro, thioalkyl, alkoxy, or hydroxy; any pair of R, R', or R" substituents may be joined to form a 4-, 5-, 6-, or 7-membered carbocyclic or heterocyclic ring; each of m and n has a value from 0 to 4; and p has a value that satisfies the valence of M. Preferably, M is a Group 4-6 transition metal, more preferably a Group 4 transition metal.

A few exemplary siloxy-bridged metallocene complexes:

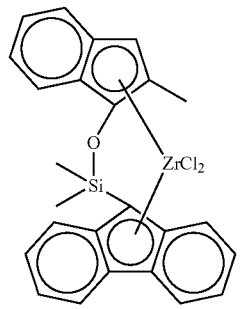

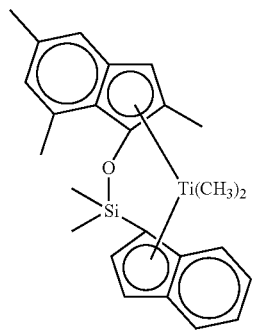

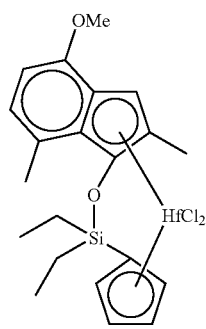

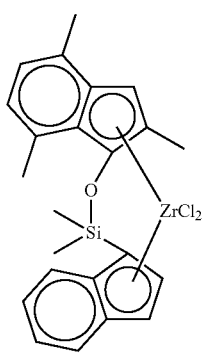

-continued

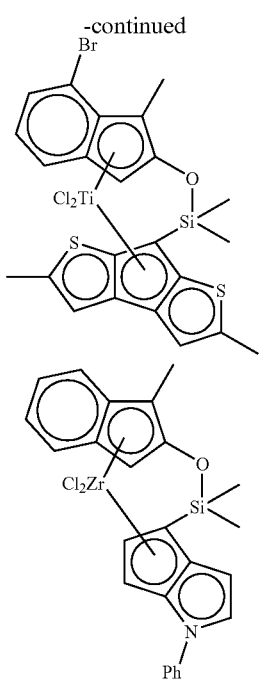

The method is particularly valuable for making complexes in which the position of the siloxy bridge is predefined. As discussed in the background section, many bridged metallocene complexes are made from indenes, usually via an indanone precursor. Unfortunately, the usual process of converting an indanone to an indene forfeits an opportunity to control regiochemistry. This is particularly important when the indanone has substituents, and deprotonation of the corresponding indene can result in more than one possible indenide anion. As noted earlier, indenes are therefore a non-ideal choice as a starting material for making a single ligand precursor and a corresponding single bridged metallocene complex.

The complex manufacturer remains in control when the target is a siloxy-bridged metallocene of the invention because a particular indanone starting material can be selected that will provide the desired regioisomer as a ligand precursor. Moreover, because a wide variety of substituted and unsubstituted 1-indanones and 2-indanones are either commercially available or readily synthesized by well-established routes, the method is exceptionally versatile. The ability to make a single regioisomer preserves the "single site" nature of the metallocene, so polyolefins made from the complex can have desirable attributes such as narrow molecular weight distribution and predictable melt-flow properties.

The inventive method provides siloxy-bridged metallocenes, a structurally similar alternative to conventional silyl-bridged complexes, in fewer reaction steps. With the usual indene approach, an indanone is reduced (or alkylated), then dehydrated, then deprotonated and converted to a silyl-bridged precursor (often a mixture of precursors), and finally converted to the transition metal complex(es). In contrast, the present method provides a particular siloxy-bridged ligand precursor directly from an indanone in a simple, one-pot process (see, e.g., Examples 1, 3, and 5 below), and gives the desired siloxy-bridged metallocene complex in one additional step (see Exs. 2, 4, and 6 below). Fewer steps translates into substantial time and cost savings for the catalyst manufacturer. In sum, the method of the invention provides a simple, regioselective approach to siloxy-bridged metallocene complexes.

The siloxy-bridged metallocenes are useful for polymerizing olefins. Suitable olefins include ethylene, propylene, 1-butene, 1-hexene, 1-octene, and the like, and mixtures thereof.

In a typical olefin polymerization, the siloxy-bridged metallocene complex is used in combination with an activator, which helps to ionize the complex and activate the catalyst. Suitable activators are well known in the art. Examples include alumoxanes (methyl alumoxane (MAO), PMAO, ethyl alumoxane, diisobutyl alumoxane), alkylaluminum compounds (triethylaluminum, diethylaluminum chloride, trimethylaluminum, triisobutylaluminum), and the like. Suitable activators include acid salts that contain non-nucleophilic anions. These compounds generally consist of bulky ligands attached to boron or aluminum. Examples include lithium tetrakis(pentafluorophenyl)borate, lithium tetrakis (pentafluorophenyl)aluminate, anilinium tetrakis(pentafluorophenyl)-borate, and the like. Suitable activators also include organoboranes, which include boron and one or more alkyl, aryl, or aralkyl groups. Suitable activators include substituted and unsubstituted trialkyl and triarylboranes such as tris(pentafluorophenyl)borane, triphenylborane, tri-n-octylborane, and the like. These and other suitable boron-containing activators are described in U.S. Pat. Nos. 5,153,157, 5,198,401, and 5,241,025. Suitable activators also include aluminoboronates—reaction products of alkyl aluminum compounds and organoboronic acids—as described in U.S. Pat. Nos. 5,414,180 and 5,648,440. Alumoxane activators, such as MAO, are preferred.

The optimum amount of activator needed relative to the amount of siloxy-bridged complex depends on many factors, including the nature of the complex and activator, the desired reaction rate, the kind of polyolefin product, the reaction conditions, and other factors. Generally, however, when the activator is an alumoxane or an alkyl aluminum compound, the amount used will be within the range of about 0.01 to about 5000 moles, preferably from about 10 to about 500 moles, and more preferably from about 10 to about 200 moles, of aluminum per mole of transition metal, M. When the activator is an organoborane or an ionic borate or aluminate, the amount used will be within the range of about 0.01 to about 5000 moles, preferably from about 0.1 to about 500 moles, of activator per mole of M. The activator can be combined with the complex and added to the reactor as a mixture, or the components can be added to the reactor separately.

The siloxy-bridged metallocene complex can be supported. Suitable supports include silicas, aluminas, silica-aluminas, titanias, styrenic polymer resins, or the like. Silica is particularly preferred. The support is preferably treated thermally, chemically, or both prior to use to reduce the concentration of surface hydroxyl groups. Thermal treatment consists of heating (or "calcining") the silica in a dry atmosphere at elevated temperature, preferably greater than about 100° C., and more preferably from about 150 to about 600° C., prior to use. A variety of different chemical treatments can be used, including reaction with organoaluminum, -magnesium, -silicon, or -boron compounds. See, for example, the techniques described in U.S. Pat. No. 6,211,311.

The siloxy-bridged complexes can be used in any of the well-known types of processes for polymerizing olefins. For example, they can be used in a slurry, solution, bulk, or gas-phase process. Supported catalysts are most useful in gas-phase or slurry polymerizations. Suitable methods for polymerizing olefins using the catalysts of the invention are described, for example, in U.S. Pat. Nos. 5,902,866, 5,637,659, and 5,539,124.

The polymerizations can be performed over a wide temperature range, such as about −30° C. to about 280° C. A more preferred range is from about 30° C. to about 180° C.; most preferred is the range from about 60° C. to about 100° C. Olefin partial pressures normally range from about 15 psia to about 50,000 psia. More preferred is the range from about 15 psia to about 1000 psia.

The following examples merely illustrate the invention. Those skilled in the art will recognize many variations that are within the spirit of the invention and scope of the claims.

EXAMPLE 1

(2-Methyl-3H-inden-1-yloxy)(fluoren-9-yl)dimethylsilane (1)

Lithium diisopropylamide (10 mL of 2M solution in THF/heptane/ethylbenzene) is added dropwise to an ice-cooled solution of 2-methylindanone (2.90 g, 20.0 mmol) in dry toluene (30 mL) under argon. Following the addition, the mixture warms to room temperature and is stirred for 3 h. The resulting cloudy, orange solution is added dropwise under argon with ice cooling to a solution of (fluoren-9-yl)chlorodimethylsilane (5.2 g, 20 mmol) in dry toluene (60 mL). After stirring overnight at room temperature, the mixture is washed twice with brine, dried, and concentrated. Column chromatography (hexane/methylene chloride, 2:1) on silica provides a yellow solid (5.4 g, 14.7 mmol, 74%), the desired indenoxy(fluorenyl)silane 1, which has a $^1$H NMR spectrum consistent with the following structure:

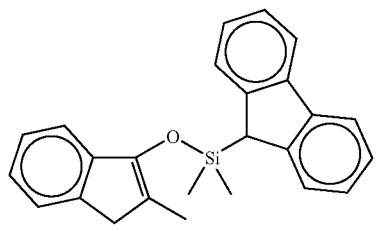

EXAMPLE 2

Dimethylsilyl(2-methylinden-1-yloxy)(fluoren-9-yl)zirconium dichloride (2)

t-Butyllithium (0.96 mL of 1.7 M solution in pentane, 1.63 mmol) is added to (2-methyl-3H-inden-1-yloxy)(fluoren-9-yl)dimethylsilane (1) (0.30 g, 0.81 mmol) in dry diethylether (20 mL) at −78° C. under argon. The resulting yellow-orange suspension of dianion stirs for 2 h at −78° C. A suspension of zirconium tetrachloride (0.19 g, 0.81 mmol) in dry pentane (5 mL) is added to the dianion. The cooling bath is removed, and the suspension stirs overnight at room temperature. The suspension is filtered, and the filtrate is concentrated. The orange residue is washed with a 1:1 mixture of diethylether/pentane (2×10 mL), then with pentane (10 mL) and dried. Yield: 0.12 g (28%). The product, siloxy-bridged zirconium complex 2, has a $^1$H NMR spectrum that is consistent with the following structure:

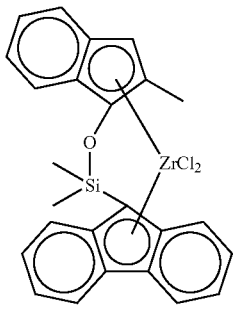

EXAMPLE 3

(2,4,7-Trimethyl-3H-inden-1-yloxy)(fluoren-9-yl)dimethylsilane (3)

Lithium diisopropylamide (3 mL of 2M solution in THF/heptane/ethylbenzene) is added dropwise to an ice-cooled solution of 2,4,7-trimethylindanone (1.0 g, 5.7 mmol) in dry toluene (10 mL) under argon. Following the addition, the mixture warms to room temperature and is stirred for 3 h. The resulting yellow solution is added dropwise under argon with ice cooling to a solution of (fluoren-9-yl)chlorodimethylsilane (1.7 g, 5.7 mmol) in dry toluene (15 mL). After stirring overnight at room temperature, the mixture is washed with brine, dried, and concentrated. Column chromatography (hexane/methylene chloride, 4:1) on silica provides a yellow solid (0.9 g, 2.3 mmol, 40%), the desired indenoxy(fluorenyl)silane 3, which has a $^1$H NMR spectrum consistent with the following structure:

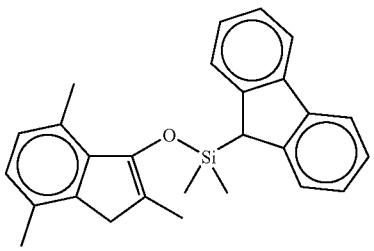

EXAMPLE 4

Dimethylsilyl(2,4,7-trimethylinden-1-yloxy)(fluoren-9-yl)zirconium dichloride (4)

t-Butyllithium (1.29 mL of 1.7 M solution in pentane, 2.20 mmol) is added to (2,4,7-trimethyl-3H-inden-1-yloxy)(fluoren-9-yl)dimethylsilane (3) (0.45 g, 1.1 mmol) in dry diethylether (20 mL) at −78° C. under argon. The resulting yellow solution of dianion stirs for 3 h at −78° C. A suspension of zirconium tetrachloride (0.25 g, 1.1 mmol) in dry pentane (5 mL) is added to the dianion. The usual isolation procedure (from Example 2) provides the desired siloxy-bridged zirconium complex 4 (yield: 0.30 g, 49%), which has a $^1$H NMR spectrum that is consistent with the following structure:

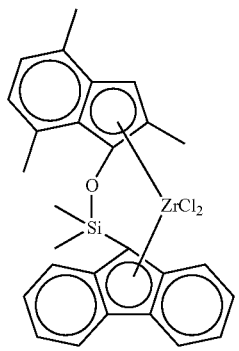

EXAMPLE 5

(2-Methyl-3H-inden-1-yloxy)(2,5-dimethyl-7H-cyclopentyl[1,2-b;4,3-b']dithiophen-7-yl)dimethylsilane (5)

Lithium diisopropylamide (0.82 g in 20 mL of dry tetrahydrofuran, 7.7 mmol) is added dropwise to an ice-cooled solution of 2-methylindanone (1.1 g, 7.7 mmol) in dry toluene (20 mL) under argon. Following the addition, the mixture warms to room temperature and is stirred for 3 h. The resulting yellow solution is added dropwise under argon with ice cooling to a solution of (2,5-dimethyl-7H-cyclopentyl[1,2-b;4,3-b']dithiophen-7-yl)dimethylchlorosilane (2.3 g, 7.7 mmol) in dry toluene (20 mL) and dry tetrahydrofuran (20 mL). After stirring overnight at room temperature, the mixture is washed with saturated aqueous ammonium chloride, dried, and concentrated. Column chromatography (hexane/methylene chloride, 4:1) on silica provides a yellow solid (1.7 g, 4.16 mmol, 54%), the desired siloxy-bridged ligand precursor 5, which has a $^1$H NMR spectrum consistent with the following structure:

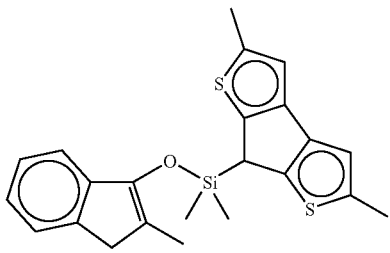

EXAMPLE 6

Dimethylsilyl(2-methyl-3H-inden-1-yloxy)(2,5-dimethylcyclopent-7-yl[1,2-b;4,3-b']dithiophenyl)zirconium dichloride (6)

t-Butyllithium (0.58 mL of 1.7 M solution in pentane, 0.98 mmol) is added to (2-methyl-3H-inden-1-yloxy)(2,5-dimethyl-7H-cyclopentyl[1,2-b;4,3-b']dithiophen-7-yl)dimethylsilane (5) (0.20 g, 0.49 mmol) in dry diethylether (30 mL) at −78° C. under argon. The resulting yellow solution of dianion stirs for 2 h at −78° C. and 30 min. after removing the cooling bath. A suspension of zirconium tetrachloride (0.11 g, 0.49 mmol) in dry pentane (3 mL) is added to the dianion. The cooling bath is removed, and the suspension stirs overnight at room temperature. The orange suspension is filtered and the filter cake is dried. The product, siloxy-bridged ziroconium complex 6, has a $^1$H NMR spectrum that is consistent with the following structure:

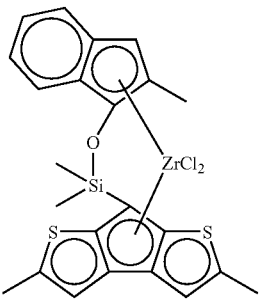

COMPARATIVE EXAMPLE 7

The procedure of Example 2 is followed except that n-butyllithium is used instead of t-butyllithium. After workup, no bridged complex is isolated. Instead, the products are 2-methylindanone and n-butyl(fluoren-9-yl)dimethylsilane.

EXAMPLE 8

Ethylene Polymerization

Methyl alumoxane (5 mL of 10 wt. % MAO in toluene) is added to a 100-mg sample of any of the siloxy-bridged complexes prepared in Examples 2, 4, or 6. The mixture is injected into a 1.7-L stainless-steel autoclave containing dry, deoxygenated isobutane (850 mL) and triisobutylaluminum (0.2 mmol). The autoclave is heated to 80° C. and is pressurized with ethylene (150 psi). After 1 h, the autoclave is cooled, isobutane is flashed off. In each case, the resulting product should be polyethylene.

The preceding examples are meant only as illustrations. The following claims define the invention.

I claim:

1. A method for making a siloxy-bridged metallocene complex, said method comprising:
   (a) reacting an indanone enolate with a cyclopentadienylsilyl compound to produce a ligand precursor; and
   (b) reacting the precursor with a Group 3-10 transition metal source to produce the metallocene complex.

2. The method of claim 1 wherein the enolate is substituted.

3. The method of claim 1 wherein the enolate is prepared from 2-methyl-1-indanone.

4. The method of claim 1 wherein the cyclopentadienylsilyl compound comprises a substituted or unsubstituted cyclopentadienyl, indenyl, fluorenyl, or thiophene-fused cyclopentadienyl group.

5. The method of claim 1 wherein the precursor is doubly deprotonated with a sterically hindered base prior to its reaction with the transition metal source.

6. The method of claim 1 wherein the complex comprises a Group 4 transition metal.

7. The method of claim 1 wherein the complex has the structure:

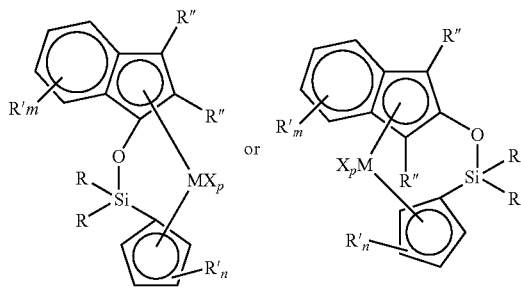

wherein M is a Group 3-10 transition metal, each X is independently selected from the group consisting of halide, hydrocarbyl, alkoxy, dialkylamino, and siloxy; each R is independently selected from the group consisting of $C_1$-$C_{20}$ hydrocarbyl, each R' is independently selected from the group consisting of hydrocarbyl, halocarbyl, halide, amino, nitro, thioalkyl, alkoxy, and hydroxy; each R" is independently selected from the group consisting of hydrogen, hydrocarbyl, or R" substituents may be joined to form a 4-, 5-, 6-, or 7-membered carbocyclic or heterocyclic ring; each of m and n has a value from 0 to 4; and p has a value that satisfies the valence of M.

8. A method for making a siloxy-bridged ligand precursor, said method comprising reacting an indanone enolate with a cyclopentadienylsilyl compound to produce the ligand precursor.

9. The method of claim 8 wherein the enolate is substituted.

10. The method of claim 8 wherein the enolate is prepared from 2-methyl-1-indanone.

11. The method of claim 8 wherein the cyclopentadienylsilyl compound comprises a substituted or unsubstituted cyclopentadienyl, indenyl, fluorenyl, or thiophene-fused cyclopentadienyl group.

12. The method of claim 8 wherein the precursor has the structure:

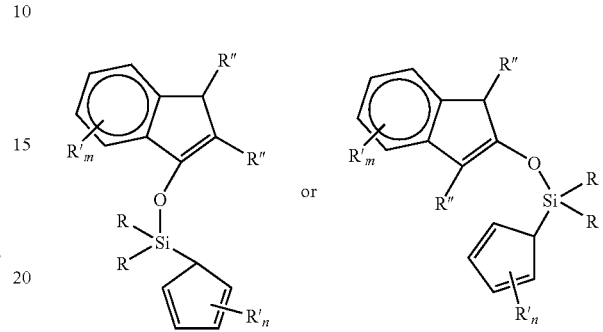

wherein each R is independently selected from the group consisting of $C_1$-$C_{20}$ hydrocarbyl, each R' is independently selected from the group consisting of hydrocarbyl, halocarbyl, halide, amino, nitro, thioalkyl, alkoxy, and hydroxy; each R" is independently selected from the group consisting of hydrogen, hydrocarbyl, halocarbyl, halide, amino, nitro, thioalkyl, alkoxy, and hydroxy; any pair of R, R', or R" substituents may be joined to form a 4-, 5-, 6-, or 7-membered carbocyclic or heterocyclic ring; and each of m and n has a value from 0 to 4.

13. A metallocene complex made by the method of claim 1.

14. A ligand precursor made by the method of claim 8.

* * * * *